United States Patent [19]

Morris

[11]  4,331,654
[45]  May 25, 1982

[54] MAGNETICALLY-LOCALIZABLE, BIODEGRADABLE LIPID MICROSPHERES

[75] Inventor: Robert M. Morris, Franklin, Ind.

[73] Assignee: Eli Lilly and Company, Indianapolis, Ind.

[21] Appl. No.: 159,321

[22] Filed: Jun. 13, 1980

[51] Int. Cl.$^3$ ............................................. A61K 9/50
[52] U.S. Cl. ........................................ 424/38; 128/1.3; 252/62.53; 424/14; 424/199
[58] Field of Search ............................. 424/14, 199, 38; 128/1.3; 252/62.53

[56] References Cited

U.S. PATENT DOCUMENTS

| | | | |
|---|---|---|---|
| 2,671,451 | 3/1954 | Bolger | 128/260 |
| 2,971,916 | 2/1961 | Schleicher et al. | 252/62.53 |
| 3,042,616 | 7/1962 | Brown | 252/62.53 |
| 3,057,344 | 10/1962 | Abella et al. | 128/260 X |
| 3,137,631 | 6/1964 | Soloway | 128/264 |
| 3,159,545 | 12/1964 | Kidwell et al. | 424/1 |
| 3,190,837 | 6/1965 | Brynko et al. | 252/316 |
| 3,474,777 | 10/1969 | Figge et al. | 128/260 X |
| 3,725,113 | 4/1973 | Chang | 424/10 X |
| 3,937,668 | 2/1976 | Zolle | 252/316 |
| 3,960,757 | 6/1976 | Morishita et al. | 424/243 X |
| 4,115,534 | 9/1978 | Ithakissios | 424/1 |
| 4,147,767 | 4/1979 | Yapel | 424/22 |
| 4,247,406 | 1/1981 | Widder et al. | 252/62.53 |

FOREIGN PATENT DOCUMENTS

2656317  12/1976  Fed. Rep. of Germany.

OTHER PUBLICATIONS

Gregoriadis, G., *New England J. Med.,* 295, 704–710 and 765–770 (1976).
Conn et al., *Outlines of Biochemistry,* 2nd Edition, John Wiley, New York, 1967, pp. 54–65.
Widder, K., et al., *Proc. Soc. Exp. Biol. Med.,* 58, 141 (1978).
Rahman, Y., et al., *Proc. Soc. Exp. Biol. Med.,* 146 1173 (1974).
Juliano, R., et al., *Biochem. Biophys. Res. Comm.,* 63(3), 651 (1975).
Gregoriadis, G., et al., *Biochem. Biophys. Res. Comm.,* 65(2), 537 (1975).
Widder, K., et al., Abstract of Paper Presented At AACR Meeting, 5/80.
Widder, K., et al., Abstract of Paper Presented at Fed. Societies Meeting, 4/80.
Wisse, E., et al., *J. Retic. Soc.,* 18, Abstract Supp. p. 10a (9/75).
Gregoriadis, G., et al., *Brit. J. Biochem.,* 24, 485 (1972).
Gregoriadis, G., et al., *Evr. Jr. Biochem.,* 47,179 (1974).
Zolle, I., et al., *Int. J. Appl. Rad. Isotopes,* 21,155 (1970).
*Chemical Abstracts,* 80:52392a (1974), [Japanese Patent 73 24,246, Takai, et al., 7/19/73].

*Primary Examiner*—Richard A. Schwartz
*Attorney, Agent, or Firm*—James L. Rowe; Arthur R. Whale

[57]  ABSTRACT

Drug carrier formulation consisting of magnetically-localizable, biodegradable lipid microspheres.

11 Claims, No Drawings

MAGNETICALLY-LOCALIZABLE, BIODEGRADABLE LIPID MICROSPHERES

BACKGROUND OF THE INVENTION

Magnetically-localizable, biodegradable albumen microspheres have been described by Widder et al., *Proc. Soc. Exp. Biol. Med.,* 58, 141 (1978). The use of such microspheres containing the anticancer drug, adriamycin, in treating rats bearing a Yoshida sarcoma is described in an abstract of a paper by Widder et al., given at the annual meeting of the American Association for Cancer Research in May of 1980 and also at the Federated Societies Meeting in San Francisco, April 1980. Magnetically-localizable, biodegradable albumen microspheres are also described and claimed in the copending application of Senyei and Widder, Ser. No. 32,399 filed Apr. 23, 1979, now U.S. Pat. No. 4,247,406.

U.S. Pat. No. 4,115,534 discloses a method for determining the concentration of various substances in biological fluids by using magnetically-responsive, permeable, solid, water-insoluble microparticles. The water-insoluble permeable solid matrix can be composed of proteinaceous materials, polysaccharides, polyurethanes or mixtures thereof. The magnetically-responsive material employed is $BaFe_{12}O_{19}$. This material is mixed with, for example, bovine serum albumen and the resulting mixture added to a solution comprising a dewatering agent, a cross-linking agent and castor oil. A dispersion of the aqueous material in the oil phase is produced thereby. Particles thus formed are employed in vitro for determining concentrations of various substances in biological fluids.

An abstract of a Japanese patent, *Chemical Abstracts,* 80, 52392a (1974), describes a magnetic material coated with an organic polymer. The combination can be used as a carrier for drugs and x-ray contrast media. For instance, if the material is given orally to an ulcer patient, the magnet localizes the iron-bearing polymer of the lesion and sharp x-ray photos are obtained. Another Japanese advance has been described in the recent press wherein microspheres of a biodegradable nature containing a drug were coated with magnetic particles and the coated microspheres are injected into an animal. The microspheres thus prepared were in excess of 10 microns in diameter.

Figge et al, U.S. Pat. No. 3,474,777, disclose and claim finely divided particles of a magnetically-responsive substance having a coating of a therapeutic agent thereon, said particles being injectable. No actual examples are given. Schleicher et al, U.S. Pat. No. 2,971,916, describe the preparation of pressure-rupturable microscopic capsules having contained therein, in suspension in a liquid vehicle, micro-fine particles of a magnetic material useful in printing. U.S. Pat. No. 2,671,451 discloses and claims a remedial pill containing a substance soluble in the human body and including a magnetically-attractable metal element. No specific materials are disclosed. U.S. Pat. No. 3,159,545 discloses a capsule formed of a non-toxic, water-soluble thermoplastic material and a radioactive composition compounded from pharmaceutical oils and waxes in the said capsule. The capsule material is usually gelatin. U.S. Pat. No. 3,190,837 relates to a minicapsule in which the core is surrounded first by a film of a hydrophylic film-forming colloid (first disclosed in U.S. Pat. No. 2,800,457) and a second and different hydrophylic film-forming colloid adherantly surrounding the core plus the first hydrophylic film. Successive deposits of capsule or wall material may also be employed. Among the core materials are mentioned a number of magnetic materials including magnetic iron oxide. A large number of oils may also be employed as core materials but these are, as far as can be seen, not pharmacologically active. Finally U.S. Pat. No. 3,042,616 relates to a process of preparing magnetic ink as an oil-in-water emulsion.

There are a number of references which employ lipid materials to encapsulate various natural products. For example, U.S. Pat. No. 3,137,631 discloses a liquid phase process for encapsulating a water-insoluble organic liquid, particularly an oil or fragrance, with albumen. The albumen coating is then denatured, and the whole aerated. Specific examples include the encapsulation of methyl benzoate, pinene or bornyl acetate and the like in egg albumen. U.S. Pat. No. 3,937,668 discloses a similar product useful for carrying radioactive drugs, insecticides, dyes, etc. Only the process of preparing the microspheres is claimed. U.S. Pat. No. 4,147,767 discloses solid serum albumen spherules having from 5 to 30% of an organic medicament homogenously entrapped therein. The spherules are to be administered intravascularly. Zolle, the patentee of U.S. Pat. No. 3,937,668 has also written a definitive article appearing in *Int. J. Appl. Radiation Isotopes,* 21, 155 (1970). The microspheres disclosed therein are too large to pass into capillaries and are ultimately abstracted from the circulation by the capillary bed of the lungs. U.S. Pat. No. 3,725,113 discloses microencapsulated detoxicants useful on the other side of a semipermeable membrane in a kidney machine. In this application of the microencapsulation art, the solid detoxicant is first coated with a semipermeable polymer membrane and secondly with a permeable outer layer consisting of a blood-compatible protein. U.S. Pat. No. 3,057,344 discloses a capsule to be inserted into the digestive tract having valve means for communicating between the interior of the capsule and exterior, said valve being actuable by a magnet. Finally, German Offenlegungsschrift, No. P. 265631 7.7 filed Dec. 11, 1976 discloses a process wherein cells are suspended in a physiological solution containing also ferrite particles. An electric field is applied thereto thereby causing hemolysis. A drug such as methotrexate is added as well as a suspension of ferrite particles. The temperature of the suspension is then raised in order to heal the hemolysed cells. The final product is a group of cells loaded with ferrite particles and containing also a drug, which cells can be directed to a target in vivo by means of a magnet.

Lipid materials, particularly liposomes have also been employed to encapsulate drugs with the object of providing an improved therapeutic response. For example, Rahman et al, *Proc. Soc. Exp. Biol. Med.,* 146, 1173 (1974) encapsulated actinomycin D in liposomes. It was found that actinomycin D was less toxic to mice in the liposome form than in the non-encapsulated form. The mean survival times for mice treated with actinomycin D in this form were increased for Ehrlich ascites tumor. Juliano and Stamp, *Biochemical and Biophysical Research Communications,* 63, 651 (1975) studied the rate of clearance of colchicine from the blood when encapsulated in a liposome and when non-encapsulated.

Among the major contributors to this area of research—use of liposomes—has been Gregoriades and his co-workers. Their first paper concerned the rate of disapparence of protein-containing liposomes injected into a rate [*Brit. J. Biochem.*, 24, 485 (1972)]. This study was continued in *Eur. J. Biochem.*, 47, 179 (1974) where the rate of hepatic uptake and catabolism of the liposome-entrapped proteins was studied. The authors believed that therapeutic enzymes could be transported via liposomes into the lysosomes of patients suffering from various lysosomal diseases. In *Biomedical and Biophysical Research Communications* 65, 537 (1975), the group studied the possibility of holding liposomes to target cells using liposomes containing an antitumor drug. The actual transport of an enzyme, horseradish peroxidase, to the liver via liposomes was discussed in an abstract for 7th International Congress of the Reticuloendothelial Society, presented at Pamplona, Spain, Sept. 15-20, 1975.

Applicant has been unable to find any reference which advocated or taught the use of magnetic particles in a biodegradable lipid microsphere to provide a pharmaceutical formulation suitable for transporting drugs to a site subject to a magnetic field.

DESCRIPTION OF THE INVENTION

This invention provides a drug carrier formulation consisting of magnetically-localizable, biodegradable lipid microspheres containing a magnetically responsive substance such as finely divided magnetite, one or more biodegradable lipids and one or more non-toxic surfactant. The microspheres of this invention should be below about $5\mu$ in size and preferably below about $3\mu$ with an average size of $1$-$2\mu$. The biodegradable lipids which can be employed in forming my novel lipid microspheres include the fatty acids, a preferred group of such fatty acids being those saturated fatty acids having an even number of carbon atoms and melting between about 30° C., just above room temperature, and 100° C. Such acids include lauric, myristic, palmitic, stearic, arachidic (eicosanic), behenic (docosanoic), erucic, brassic, and the like as well as mixtures thereof. It should be noted that the lower melting unsaturated fatty acids such as linoleic, oleic and the like can also be used in admixture with one of the above saturated fatty acids as long as the final lipid mixture melts in the range from 30°-100° C.

Other lipid constituents which are useful in my invention include high molecular weight alcohols such as myristyl (n-tetradecyl), cetyl (n-octadecyl) and the like; and mono, di and triglycerides including glycerol esters of any of the above listed aliphatic acids such as oleic and palmitic. As before, it is a requirement of the lipid microspheres of this invention that the microspheres themselves melt below about 100° C. and solidify above about 30° C. Thus, the triglyceride components of such lipid microspheres may melt in the acceptable range, but if they melt outside of the acceptable range, mixtures thereof with other substances melting within the acceptable range are employed to lower the melting point to a temperature within the 30°-100° C. range.

Other classes of high molecular weight lipid substances useful in this invention include the phospholipids, including lecithin; sterols including cholesterol, the sitosterols, stigmasterol and the like (these sterols when purified melt well above 100° C. and must be used in admixture with other substances so as to decrease the melting point of the mixture to below about 100° C.); sterol-like substances such as lanosterol, and the cerebrosides, containing a base, a fatty acid and a sugar. Among the more common cerebrosides are phrenosin and kerasin.

The finely divided magnetically responsive particles which are present in my novel drug carriers are preferably particles of magnetite or magnetic oxide of iron, $Fe_3O_4$. Any metal, or metal salt however which can be drawn to one of the poles of a magnet is utilizable in my magnetically-localizable lipid microspheres. The magnetic particles to be used in preparing the lipid microspheres of this invention should be in an ultra-fine state of subdivision, having an average size not to exceed 1000 Å and preferably an average size of not over 300 Å. Fine powders or suspensions of magnetite having a size range from 100-200 Å are commercially available. If particles of a smaller average size are desirable, they can be readily prepared by conventional means such as ball-milling.

Surfactants which I have found operative in the preparation of my novel magnetically-localizable, biodegradable microspheres include such non-ionic surfactants as polyoxyethylene sorbitan mono-oleate. While non-ionic surfactants are preferable because of lesser reactivity and broader compatability, anionic and cationic surfactants can also be employed. Anionic "soaps" such as sodium palmitate or oleate, sulfates of long-chain aliphatic alcohols such as sodium lauryl sulfate, and sulfonated esters such as sodium sulfoethyl oleate can be utilized. Likewise, cationic surfactants such as the quarternary ammonium salts can be employed; e.g. doderyl benzyl dimethyl ammonium chloride and N-alkyl isoquinolinium salts. Naturally occurring surface active agents such as the lecithins are also operative.

As previously stated, while the precise nature of the surfactant is not critical to the preparation of my novel microspheres, the presence of a surfactant is critical as will be seen from the following general directions for the preparation of the microspheres themselves. First the lipid materials, surfactants and magnetite are weighed out. The magnetite is wetted with the surfactant and part of the lipid materials. The magnetite thus wetted is then added to the remaining lipid components and the mixture brought to a temperature of about 90°-100° C. At this temperature, all the components should be completely melted/dissolved (except for the magnetite which is in suspension). The lipid mixture is then added to a predetermined quantity of water which had been previously heated to the same 90°-100° C. temperature. After mixing, this lipid/water (oil-in-water emulsion) is sonicated to form a microemulsion, using a Branson W-185D sonicator for 2-3 minutes at 90°-100° C. While continuing the sonication, the emulsion is cooled to a temperature below the solidification point of the microspheres. This solidification point should be above room temperature so that the lipids will not melt under ordinary handling. A melting temperature above about 30° C. is satisfactory. The water phase is then removed by lyophilization. Lipid microspheres thus produced are usually $4\mu$ or below in size and have a somewhat higher content of iron than that present in the initial mixture.

Microsphere size is determined by degree of sonication and maintenance of small size during cooling of the lipid droplets to the point where solid microspheres are formed. Microspheres of a diameter greater than $5\mu$ or lower size if desired can be removed by ultra filtration using a micropore filter of suitable size.

The lipid microspheres of this invention are useful for carrying drugs to specific sites in the body. For example, lipid microspheres prepared according to the procedure of this invention and carrying an oncolytic agent, can be injected intra-arterially upstream from a tumor having a single blood supply. The magnetically-localizable lipid microspheres are then localized in the tumor by applying a magnet in close proximity thereto. The procedure here is the same as that described by Widder et al., *Proc. Soc. Exp. Biol. Med.*, 58, 141 (1978) for localizing similar magnetically-localizable microspheres prepared from a hydrophyllic material, bovine serum albumin.

Drugs which can be incorporated in the lipid microspheres of this invention include such fat-soluble materials as adriamycin base, vindesine base, benoxaprofen base, methotrexate, frentizole, prednisolone, betamethasone and the like. In other words, any of the known steroids, antiarthritic agents, anti-inflammatory agents, oncoloytic agents and the like which are fat-soluble and therefore capable of being coascervated by the above procedure can be incorporated into my novel lipid microspheres by simply adding from 2 to 15% of the drug by weight to the initial lipid mixture to which is added the surfactant and lipid coated magnetite prior to heating the mixture above the melting point of the constituents (except magnetite). It should be noted, of course, that drugs which decompose below the melting point of the particular lipid mixture employed cannot be profitably used with my novel drug carrier system.

The lipid materials employed in preparing my novel microspheres are biodegradable; that is to say, the mammalian body into which they are to be injected intra-arterially in order to carry a drug to a predetermined site must be able to remove them either by metabolization, phagocytocis or other method of elimination. Fatty substances which are not metabolizable or otherwise capable of being readily removed by the mammalian organism include petroleum fractions, mineral oil and the like. Such are not useful in this invention.

The following is a specific example of the preparation of magnetically-localizable, biodegradable lipid microspheres according to this invention.

EXAMPLE 1

110 mg. of a dried magnetite dispersion (obtained commercially as an aqueous suspension containing a surfactant and finely divided $Fe_3O_4$ of 400 gauss saturation prior to drying) was throughly wetted with a mixture of 45 mg. of polyoxyethylene sorbitan mono-oleate and 45 mg. of linoleic acid. The magnetite thus wetted was added to a mixture of 396 mg. of palmitic acid and 45 mg. of L-alpha-lecithin. The combined components were heated to about 90° C. at which point they were completely melted or dissolved (except for the magnetite which was in suspension). This lipid mixture was added to 50 ml. of water also heated to about 90° C. The lipid/water mix was then sonicated using a Branson W-185D sonicator equipped with a $\frac{1}{4}''$ titanium probe. Sonication at 100 watts for 2–3 minutes produced a satisfactory microemulsion. Sonication was adjusted to 50 watts and the temperature allowed to fall until the microspheres solidified. Water was removed therefrom by lyophilization to form a microemulsion. Sonication was continued while the temperature of the microemulsion was allowed to drop to a temperature at which the lipid microspheres resolidified—approximately 40° C. The water was then lyophilized from the emulsion leaving the lipid microspheres as discrete particles. Particle size determined via microscopy indicated no particles larger than $3\mu$ in diameter. An iron assay by atomic absorption spectroscopy indicated about 19% $Fe_3O_4$.

One or more drugs can be incorporated into lipid microspheres formed as above by adding the drug in a fat-soluble form to the mixture of lipid ingredients before addition of the wetted magnetite. The amount of any given drug which can be incorporated into my novel lipid microspheres will, of course, be dependant on the solubility of the drug in the particular lipid material.

I claim:

1. A magnetically-localizable, biodegradable, substantially water-free drug carrier formulation consisting essentially of lipid microspheres containing a magnetically-responsive substance, one or more biodegradable lipids and one or more non-toxic surfactants.

2. Microspheres according to claim 1 in which the magnetically-responsive substance is finely divided magnetite.

3. Microspheres according to claim 2 in which the magnetite particles have an average size less than 1000 Å.

4. Microspheres according to claim 1 in which one of the lipids is a fatty acid having an even number of carbon atoms.

5. Microspheres according to claim 1 melting in the range 30°–100° C.

6. Microspheres according to claim 1 in which one or more non-ionic surfactants is employed.

7. Microspheres according to claim 1 in which the average particle size is less than $4\mu$.

8. Microspheres according to claim 1 of less than $5\mu$ in diameter.

9. Microspheres according to claim 1 comprising palmitic acid, magnetite particles of average size less than 1000 Å, lecithin and polyoxy ethylene sorbitan mono-oleate having an average size of less than about $4\mu$.

10. A magnetically-localizable, biodegradable drug carrier formulation consisting of a lipid soluble drug dispersed in lipid microspheres, substantially free of water, said lipid microspheres being composed of one or more biodegradable lipids, a magnetically responsive substance and one or more non-toxic surfactants.

11. A drug carrier formulation according to claim 10 in which the drug is an oncolytic agent.

* * * * *